(12) United States Patent
Pinedjian

(10) Patent No.: US 8,177,747 B2
(45) Date of Patent: May 15, 2012

(54) METHOD AND APPARATUS FOR DRUG DELIVERY

(75) Inventor: Raffi S. Pinedjian, Fountain Valley, CA (US)

(73) Assignee: Alcon Research, Ltd., Forth Worth, TX (US)

( * ) Notice: Subject to any disclaimer, the term of this patent is extended or adjusted under 35 U.S.C. 154(b) by 0 days.

(21) Appl. No.: 12/956,195

(22) Filed: Nov. 30, 2010

(65) Prior Publication Data

US 2011/0152767 A1 Jun. 23, 2011

Related U.S. Application Data

(60) Provisional application No. 61/289,024, filed on Dec. 22, 2009.

(51) Int. Cl.
*A61M 5/44* (2006.01)
(52) U.S. Cl. ............. 604/113; 604/64; 604/84; 604/291
(58) Field of Classification Search .............. 604/57–60, 604/70, 82–85, 113, 124, 184, 187, 193, 604/196–198, 218, 221, 222, 228, 235
See application file for complete search history.

(56) References Cited

U.S. PATENT DOCUMENTS

| 640,868 | A | 1/1900 | Bring |
|---|---|---|---|
| 1,039,591 | A | 9/1912 | Prideaux |
| 1,252,614 | A | 1/1918 | Pieper |
| 1,609,424 | A | 12/1926 | Paul |
| 2,591,457 | A | 4/1952 | Maynes |
| 2,661,871 | A | 12/1953 | Huenergardt |
| 2,826,339 | A | 3/1958 | Maillard |
| 2,847,996 | A | 8/1958 | Cohen et al. |
| 3,089,815 | A | 5/1963 | Lieb et al. |
| 3,166,221 | A | 1/1965 | Nielsen |
| 3,199,740 | A | 8/1965 | Huffa et al. |
| 3,311,265 | A | 3/1967 | Creighton, Jr. et al. |
| 3,416,530 | A | 12/1968 | Ness |
| 3,439,675 | A | 4/1969 | Cohen |

(Continued)

FOREIGN PATENT DOCUMENTS

CA 1313802 2/1993

(Continued)

OTHER PUBLICATIONS

Business Wire Via First!, "Bausch & Lomb and Control Delivery Systems Agree to Develop Breakthrough Therapeutic Products for Severe Eye Diseases," NewsEdge Corp., Jun. 15, 1989, 4 pgs.

(Continued)

*Primary Examiner* — Quynh-Nhu H Vu
(74) *Attorney, Agent, or Firm* — Russell Henrichs

(57) ABSTRACT

Disposable injection devices are disclosed herein. In an exemplary arrangement, the disposable injection device comprises an annular sleeve, a predetermined pre-injection quantity of a substance configured for selective injection, and a temperature control element. The annular sleeve at least partially defines a dispensing chamber therein. The predetermined pre-injection quantity of the substance configured for selective injection is disposed within the dispensing chamber. The temperature control element is operably connected to the dispensing chamber, and is configured to selectively heat the substance to a predetermined temperature. The substance expands from the pre-injection quantity at the predetermined temperature to an injection quantity whereby the injection quantity is greater than a volume defined by the dispensing chamber. In this manner, a predetermined minimum quantity of the substance is self-expelled from the dispensing chamber.

20 Claims, 6 Drawing Sheets

U.S. PATENT DOCUMENTS

| | | | |
|---|---|---|---|
| 3,608,549 A | 9/1971 | Merrill | |
| 3,767,085 A | 10/1973 | Cannon et al. | |
| 3,828,777 A | 8/1974 | Ness | |
| 3,828,980 A | 8/1974 | Creighton et al. | |
| 3,835,835 A | 9/1974 | Thompson et al. | |
| 3,858,581 A | 1/1975 | Kamen | |
| 3,892,537 A | 7/1975 | Gulati et al. | |
| 3,952,920 A | 4/1976 | Bergman | |
| 3,982,537 A | 9/1976 | Bucalo | |
| 4,007,742 A | 2/1977 | Banko | |
| 4,014,335 A | 3/1977 | Arnold | |
| 4,030,499 A | 6/1977 | Bucalo | |
| 4,046,288 A | 9/1977 | Bergman | |
| 4,054,138 A | 10/1977 | Bucalo | |
| 4,060,083 A * | 11/1977 | Hanson | 604/59 |
| 4,109,653 A | 8/1978 | Kozam et al. | |
| 4,122,850 A | 10/1978 | Bucalo | |
| 4,161,882 A * | 7/1979 | Golch | 60/527 |
| 4,184,510 A | 1/1980 | Murry et al. | |
| 4,246,932 A | 1/1981 | Raines | |
| 4,260,077 A | 4/1981 | Schroeder | |
| 4,265,618 A | 5/1981 | Herskovitz et al. | |
| 4,300,557 A | 11/1981 | Refojo et al. | |
| 4,327,725 A | 5/1982 | Cortese et al. | |
| 4,357,136 A * | 11/1982 | Herskovitz et al. | 433/224 |
| 4,367,737 A | 1/1983 | Kozam et al. | |
| 4,392,827 A | 7/1983 | Martin | |
| 4,453,934 A | 6/1984 | Gahwiler et al. | |
| 4,464,174 A | 8/1984 | Ennis | |
| 4,471,888 A | 9/1984 | Herb et al. | |
| 4,474,752 A | 10/1984 | Haslam et al. | |
| 4,484,915 A | 11/1984 | Tartaglia | |
| 4,582,488 A | 4/1986 | Newman | |
| 4,608,042 A | 8/1986 | Vanderveen et al. | |
| 4,609,371 A | 9/1986 | Pizzino | |
| 4,610,666 A | 9/1986 | Pizzino | |
| 4,684,344 A | 8/1987 | Brockway et al. | |
| 4,704,088 A | 11/1987 | Newman | |
| 4,713,446 A | 12/1987 | DeVore et al. | |
| 4,759,746 A | 7/1988 | Straus | |
| 4,764,165 A | 8/1988 | Reimels et al. | |
| 4,792,329 A | 12/1988 | Schreuder | |
| 4,795,423 A | 1/1989 | Osterholm | |
| 4,830,855 A | 5/1989 | Stewart | |
| 4,834,714 A | 5/1989 | Lascar et al. | |
| 4,853,224 A | 8/1989 | Wong | |
| 4,911,161 A | 3/1990 | Schechter | |
| 4,911,328 A | 3/1990 | Keller | |
| 4,946,450 A | 8/1990 | Erwin | |
| 4,949,874 A | 8/1990 | Fiedler | |
| 4,992,045 A | 2/1991 | Beisel | |
| 4,997,652 A | 3/1991 | Wong | |
| 5,000,955 A | 3/1991 | Gould et al. | |
| 5,005,735 A | 4/1991 | Keller | |
| 5,066,276 A | 11/1991 | Wang | |
| 5,120,307 A | 6/1992 | Wang | |
| 5,127,831 A | 7/1992 | Bab | |
| 5,147,647 A | 9/1992 | Darougar | |
| 5,164,188 A | 11/1992 | Wong | |
| 5,167,618 A | 12/1992 | Kershner | |
| 5,174,475 A | 12/1992 | Day et al. | |
| 5,178,635 A | 1/1993 | Gwon et al. | |
| 5,224,628 A | 7/1993 | Keller | |
| RE34,487 E | 12/1993 | Keller | |
| 5,290,259 A | 3/1994 | Fischer | |
| 5,300,114 A | 4/1994 | Gwon et al. | |
| 5,322,691 A | 6/1994 | Darougar et al. | |
| 5,324,305 A | 6/1994 | Kanner | |
| 5,328,481 A | 7/1994 | Wang | |
| 5,336,175 A | 8/1994 | Mames | |
| 5,360,413 A | 11/1994 | Leason et al. | |
| 5,370,630 A | 12/1994 | Smidebush et al. | |
| 5,378,475 A | 1/1995 | Smith et al. | |
| 5,403,901 A | 4/1995 | Namdaran et al. | |
| 5,423,752 A | 6/1995 | Haber et al. | |
| 5,431,630 A | 7/1995 | Leonard | |
| 5,443,505 A | 8/1995 | Wong et al. | |
| 5,454,268 A | 10/1995 | Kim | |
| 5,466,466 A | 11/1995 | Muller | |
| 5,476,511 A | 12/1995 | Gwon et al. | |
| 5,478,323 A | 12/1995 | Westwood et al. | |
| 5,487,725 A | 1/1996 | Peyman | |
| 5,516,522 A | 5/1996 | Peyman et al. | |
| 5,568,883 A | 10/1996 | Cataneo et al. | |
| 5,582,595 A | 12/1996 | Haber et al. | |
| 5,584,815 A | 12/1996 | Pawelka et al. | |
| 5,602,188 A | 2/1997 | Nakanishi | |
| 5,620,700 A | 4/1997 | Berggren et al. | |
| 5,632,984 A | 5/1997 | Wong et al. | |
| 5,662,612 A | 9/1997 | Niehoff | |
| 5,665,069 A | 9/1997 | Cumer et al. | |
| 5,679,666 A | 10/1997 | Clark | |
| 5,722,956 A | 3/1998 | Sims et al. | |
| 5,725,493 A | 3/1998 | Avery et al. | |
| 5,743,274 A | 4/1998 | Peyman | |
| 5,743,886 A | 4/1998 | Lynn et al. | |
| 5,766,242 A | 6/1998 | Wong et al. | |
| 5,766,619 A | 6/1998 | Aiache et al. | |
| 5,770,592 A | 6/1998 | Clark | |
| 5,773,019 A | 6/1998 | Ashton et al. | |
| 5,783,205 A | 7/1998 | Berggren et al. | |
| 5,792,103 A | 8/1998 | Schwartz et al. | |
| 5,797,898 A | 8/1998 | Santini, Jr. et al. | |
| 5,817,075 A | 10/1998 | Guingo | |
| 5,824,072 A | 10/1998 | Wong | |
| 5,824,073 A | 10/1998 | Peyman | |
| 5,830,173 A | 11/1998 | Avery et al. | |
| 5,836,935 A | 11/1998 | Ashton et al. | |
| 5,860,949 A | 1/1999 | Chen | |
| 5,882,338 A | 3/1999 | Gray | |
| 5,902,598 A | 5/1999 | Chen et al. | |
| 5,904,144 A | 5/1999 | Hammang et al. | |
| 5,916,584 A | 6/1999 | O'Donoghue et al. | |
| 5,928,197 A | 7/1999 | Niehoff | |
| 5,928,663 A | 7/1999 | Peyman | |
| 5,954,695 A | 9/1999 | Sims et al. | |
| 5,971,953 A * | 10/1999 | Bachynsky | 604/90 |
| 5,984,889 A | 11/1999 | Christ et al. | |
| 6,001,386 A | 12/1999 | Ashton et al. | |
| 6,028,099 A | 2/2000 | de Juan, Jr. | |
| 6,047,861 A | 4/2000 | Vidal et al. | |
| 6,051,011 A | 4/2000 | Weidenbenner | |
| 6,074,661 A | 6/2000 | Olejnik et al. | |
| 6,126,687 A | 10/2000 | Peyman | |
| 6,135,984 A | 10/2000 | Dishler | |
| 6,165,190 A | 12/2000 | Nguyen | |
| 6,210,357 B1 | 4/2001 | Morris | |
| 6,221,045 B1 | 4/2001 | Duchon et al. | |
| 6,270,343 B1 | 8/2001 | Martin | |
| 6,290,690 B1 | 9/2001 | Huculak et al. | |
| 6,299,603 B1 | 10/2001 | Hecker et al. | |
| 6,352,522 B1 | 3/2002 | Kim et al. | |
| 6,364,865 B1 | 4/2002 | Lavi et al. | |
| 6,372,245 B1 | 4/2002 | Bowman et al. | |
| 6,378,526 B1 | 4/2002 | Bowman et al. | |
| 6,397,849 B1 | 6/2002 | Bowman et al. | |
| 6,413,245 B1 | 7/2002 | Yaacobi et al. | |
| 6,416,777 B1 | 7/2002 | Yaacobi | |
| 6,419,656 B1 | 7/2002 | Vetter et al. | |
| 6,436,143 B1 | 8/2002 | Ross et al. | |
| 6,488,659 B1 | 12/2002 | Rosenman | |
| 6,520,930 B2 | 2/2003 | Critchlow et al. | |
| 6,537,246 B1 | 3/2003 | Unger et al. | |
| 6,569,113 B2 | 5/2003 | Wirt et al. | |
| 6,585,700 B1 | 7/2003 | Trocki et al. | |
| 6,595,979 B1 | 7/2003 | Epstein et al. | |
| 6,613,024 B1 | 9/2003 | Gargione | |
| 6,635,267 B1 | 10/2003 | Miyoshi et al. | |
| 6,645,179 B1 | 11/2003 | Ishikawa et al. | |
| 6,723,074 B1 | 4/2004 | Halseth | |
| 6,726,654 B2 | 4/2004 | Rosenman | |
| 6,732,887 B2 | 5/2004 | Bills | |
| 6,940,209 B2 | 9/2005 | Henderson | |
| 6,991,457 B2 * | 1/2006 | Kazen et al. | 433/32 |
| 7,176,030 B2 | 2/2007 | Faries, Jr. et al. | |
| 7,762,981 B2 | 7/2010 | Dacquay et al. | |
| 7,815,603 B2 | 10/2010 | Dacquay et al. | |

| | | |
|---|---|---|
| 7,871,399 B2 | 1/2011 | Dacquay et al. |
| 7,887,517 B2 | 2/2011 | Santos et al. |
| 7,887,521 B2 | 2/2011 | Dacquay et al. |
| 2002/0042591 A1 | 4/2002 | Muhlbauer et al. |
| 2002/0055720 A1 | 5/2002 | Hohlfelder et al. |
| 2003/0055380 A1 | 3/2003 | Flaherty |
| 2003/0125665 A1 | 7/2003 | Rosenman |
| 2004/0013704 A1 | 1/2004 | Kabra et al. |
| 2004/0039253 A1 | 2/2004 | Peyman et al. |
| 2004/0052761 A1 | 3/2004 | Vernon et al. |
| 2004/0054319 A1 | 3/2004 | Langley et al. |
| 2004/0064102 A1 | 4/2004 | Yamada |
| 2004/0133155 A1 | 7/2004 | Varner et al. |
| 2004/0167466 A1 | 8/2004 | Drasler et al. |
| 2004/0167480 A1 | 8/2004 | Bos |
| 2004/0176720 A1 | 9/2004 | Kipfer |
| 2004/0210200 A1 | 10/2004 | Gerondale et al. |
| 2004/0231667 A1 | 11/2004 | Horton et al. |
| 2005/0015056 A1 | 1/2005 | Duchon et al. |
| 2005/0065477 A1 | 3/2005 | Jost |
| 2005/0177137 A1 | 8/2005 | Kipfer |
| 2006/0047250 A1 | 3/2006 | Hickingbotham |
| 2006/0110428 A1 | 5/2006 | deJuan et al. |
| 2007/0016186 A1 | 1/2007 | LoRusso |
| 2007/0038174 A1 | 2/2007 | Hopkins |
| 2007/0060887 A1 | 3/2007 | Marsh et al. |
| 2007/0142769 A1 | 6/2007 | Griffiths et al. |
| 2007/0244442 A1 | 10/2007 | Chowan |
| 2007/0268340 A1 | 11/2007 | Dacquay et al. |
| 2007/0270744 A1 | 11/2007 | Dacquay et al. |
| 2007/0270750 A1 | 11/2007 | Dacquay et al. |
| 2007/0282282 A1 | 12/2007 | Kaern et al. |
| 2007/0293820 A1 | 12/2007 | Dacquay et al. |
| 2008/0015545 A1 | 1/2008 | Sanchez, Jr. |
| 2008/0021412 A1 | 1/2008 | Dos Santos et al. |
| 2008/0021413 A1* | 1/2008 | Dos Santos et al. .......... 604/218 |
| 2008/0021419 A1 | 1/2008 | Dacquay et al. |
| 2008/0021438 A1 | 1/2008 | Dacquay et al. |
| 2008/0097379 A1 | 4/2008 | Dacquay et al. |
| 2008/0161757 A1 | 7/2008 | Nayak et al. |
| 2008/0281292 A1 | 11/2008 | Hickingbotham et al. |
| 2009/0036827 A1* | 2/2009 | Cazzini .......................... 604/60 |
| 2009/0036842 A1 | 2/2009 | Pinedjian |
| 2009/0036846 A1 | 2/2009 | Dacquay et al. |
| 2009/0093788 A1* | 4/2009 | Sanchez et al. ............... 604/506 |
| 2009/0093789 A1* | 4/2009 | Dacquay et al. ............... 604/506 |
| 2009/0177182 A1 | 7/2009 | Hickingbotham et al. |
| 2009/0227979 A1* | 9/2009 | Sanchez, Jr. ................... 604/506 |
| 2009/0254045 A1 | 10/2009 | Jost |
| 2009/0287150 A1 | 11/2009 | Dacquay et al. |
| 2010/0030136 A1 | 2/2010 | Dacquay et al. |
| 2010/0057003 A1 | 3/2010 | Dos Santos |
| 2010/0069842 A1 | 3/2010 | Dos Santos et al. |
| 2010/0106083 A1 | 4/2010 | Dacquay et al. |
| 2010/0106089 A1 | 4/2010 | Santos et al. |
| 2010/0137785 A1 | 6/2010 | Lind |
| 2010/0152676 A1 | 6/2010 | Clements et al. |
| 2010/0160870 A1 | 6/2010 | Clements et al. |
| 2010/0211044 A1 | 8/2010 | Dacquay et al. |
| 2010/0286632 A1 | 11/2010 | Dos Santos et al. |
| 2010/0286654 A1 | 11/2010 | Dos Santos et al. |

FOREIGN PATENT DOCUMENTS

| | | |
|---|---|---|
| DE | 3434930 A1 | 4/1986 |
| EP | 0348146 A1 | 12/1989 |
| EP | 0356372 A2 | 2/1990 |
| EP | 0356372 A3 | 3/1990 |
| EP | 0398394 A2 | 11/1990 |
| EP | 0398394 A3 | 12/1990 |
| EP | 0520443 A2 | 12/1992 |
| EP | 0398394 B1 | 10/1993 |
| EP | 0520443 A3 | 3/1994 |
| EP | 0356372 B1 | 6/1994 |
| EP | 0520443 B1 | 1/1997 |
| EP | 0904787 A1 | 3/1999 |
| EP | 1704840 A1 | 9/2006 |
| EP | 1704840 B1 | 1/2008 |
| GB | 1551767 | 8/1979 |
| JP | 2002/059055 A | 2/2002 |
| WO | WO 82/03761 A1 | 11/1982 |
| WO | WO 87/00029 A1 | 1/1987 |
| WO | WO 93/20784 A1 | 10/1993 |
| WO | WO 94/05257 A1 | 3/1994 |
| WO | WO 95/26734 A1 | 10/1995 |
| WO | WO 95/28984 A1 | 11/1995 |
| WO | WO 96/03978 A1 | 2/1996 |
| WO | WO 96/36377 A1 | 11/1996 |
| WO | WO 98/24504 A2 | 6/1998 |
| WO | WO 98/24504 A3 | 8/1998 |
| WO | WO 99/07418 A2 | 2/1999 |
| WO | WO 99/11244 A1 | 3/1999 |
| WO | WO 99/07418 A3 | 6/1999 |
| WO | WO 99/33853 A2 | 7/1999 |
| WO | WO 99/33853 A3 | 9/1999 |
| WO | WO 99/45920 A2 | 9/1999 |
| WO | WO 99/45920 A3 | 10/1999 |
| WO | WO 99/65548 A1 | 12/1999 |
| WO | WO 00/07530 A2 | 2/2000 |
| WO | WO 00/07565 A2 | 2/2000 |
| WO | WO 00/07530 A3 | 3/2000 |
| WO | WO 00/07565 A3 | 5/2000 |
| WO | WO 00/07530 A8 | 8/2000 |
| WO | WO 00/74752 A1 | 12/2000 |
| WO | WO 01/10482 A1 | 2/2001 |
| WO | WO 02/07658 A1 | 1/2002 |
| WO | WO 01/10482 A9 | 9/2002 |
| WO | WO 03/006098 A1 | 1/2003 |
| WO | WO 2004/030729 A1 | 4/2004 |
| WO | WO 2005/027578 A1 | 3/2005 |
| WO | WO 2006/037969 A1 | 4/2006 |
| WO | WO 2006/050008 A1 | 5/2006 |
| WO | WO 2006/067480 A1 | 6/2006 |
| WO | WO 2006/068921 A2 | 6/2006 |
| WO | WO 2006/108026 A2 | 10/2006 |
| WO | WO 2008/105954 A2 | 9/2008 |
| WO | WO 2008/108886 A2 | 9/2008 |
| WO | WO 2008/108886 A3 | 11/2008 |
| WO | WO 2008/105954 A3 | 3/2009 |
| WO | WO 2006/068921 A3 | 4/2009 |

OTHER PUBLICATIONS

Sidorenko, et al., "Method of Placing Irrigation System into Tenon's Space," Abstract of Russian Patent No. RU2123314, Patent Publication date Dec. 20, 1998, 1 pg.

Nesterov, et al., "A New Method for Posterior Sub-Tenon's Drug "Administration, Ophthalmic Surgery, vol. 24, No. 1, Jan. 1993, 3 pgs.

Smith, et al., Uveitis: A Clinical Approach to Diagnosis and Management (Second Edition), Copyright 1989, 28 pages.

Roman, et al., "Sub-Tenon's Anaesthesia: An Efficient and Safe Technique,"British Journal of Ophthalmology, 81:8, 1997, 4 pages.

P.A. Guise, "Single Quadrant Sub-Tenon's Block: Evaluation of a New Local Anaesthetic Technique for Eye Surgery," Anaesthesia and Intens Care, 24:241-244, Apr. 1996, 4 pages.

Stevens, "Curved, Sub-Tenon Cannula for Local Anesthesia," Ophthalmic Surgery, 24: 121-122, Feb. 1993, 2 pages.

Muthusamy, et al., "A Modified Sub-Tenon's Cannula for Local Anesthesia,"Asia-Pacific Journal of Ophthalmology, vol. 8, No. 3, Jul. 1996, 6 pages.

Katena Products, Inc., Katena Eye Instruments, Catalog Supplement, 1997, 3 pages.

Hansen, et al., "Ocular Anesthesia for Cataract Surgery: A Direct Sub-Tenon's Approach," Ophthalmic Surgery, vol. 21, No. 10, Oct. 1990, 4 pages.

Mein, et al., "Local Anesthesia for Vitreoretinal Surgery," Retina, 10:47-49, 1990, 3 pages.

Freeman, et al., "Echocardiograph Localization of Corticosteriod after Periocular Injection,"American Journal of Ophthalmology, vol. 100, No. 10, Oct. 1993, 5 pages.

Buys, et al., "Prospective Study of Sub-Tenon's versus Retrobulbar Anesthesia for Inpatient and Day-Surgery Trabeculectomy," Ophthalmology, vol. 100, No. 10, Oct. 1993, 5 pages.

Dialog File 266-FIDRIP database record; Identifying No. 122098; "Implantation of a Sub-Tenon Drug Delivery Device Loaded with a Test Article in Rabbits and Distribution of the Test Article in Ocular Tissues;" Compiled and distributed by NTIS, Jun. 3, 1999, 1 page.

Mendez, Internet printouts for Eagle Laboratories Tri-Port Sub-Tenon 100-19, 100-19c, 100-21C cannulas, Oct. 26, 1992, 1 page.

Uthoff, Internet printouts for Moria, Inc. 111275 G (25G Retrobulbar Curved, 121278 (19G Sub-Tenon) cannulas, Dec. 9, 1996, 1 page.

Ultra™ 2800 Positive Displacement; 2004; EFD, Inc. Brochure XP 1104 vol. 11.10; 2 pages.

Parker, "Your Resource for Motion and Fluid Control Components, Systems and Solutions," 8 pages.

Sanchez, Robert, "Multiple Chamber Drug Delivery," U.S. Appl. No. 12/536,527, filed Aug. 9, 2006, 30 pages.

* cited by examiner

METHOD AND APPARATUS FOR DRUG DELIVERY

PRIORITY CLAIM

This application claims the benefit of priority of U.S. Provisional Patent Application Ser. No. 61/289,024 titled "METHOD AND APPARATUS FOR DRUG DELIVERY," filed on Dec. 22, 2009, whose inventor is Raffi S. Pinedjian, which is hereby incorporated by reference in its entirety as though fully and completely set forth herein.

TECHNICAL FIELD

The present disclosure relates to methods and apparatuses for drug delivery systems. More specifically, the present disclosure relates to expelling a drug formulation from a delivery apparatus through thermal expansion.

BACKGROUND

Several diseases and conditions of the posterior segment of the eye threaten vision. Age related macula degeneration (ARMD), choroidal neovascularization (CNV), retinopathies (e.g. diabetic retinopathy, vitreoretinopathy), retinitis (e.g., cytomegalovirus (CMV) retinitis), uveitis, macular edema, glaucoma, and neuropathies are several examples.

These, and other diseases, can be treated by injecting drug formulations into the eye. Such injections are typically manually performed using a conventional syringe and needle. FIG. 1 is a perspective view of a prior art syringe used to inject drugs into the eye. In FIG. 1, the syringe includes a needle 105, a luer hub 110, a chamber 115, a plunger 120, a plunger shaft 125, and a thumb rest 130. As is commonly known, the drug to be injected is located in chamber 115. Pushing on the thumb rest 130 axially displaces the plunger, causing the plunger 120 to expel the drug through needle 105.

In using such a syringe, the surgeon is required to pierce the eye tissue with the needle, hold the syringe steady, and actuate the syringe plunger (with or without the help of a nurse) to inject the drug formulation into the eye. However, such a configuration results in uncontrolled flow rates. Further, reading the vernier is subject to parallax error which may affect the precision and accuracy of the injected volume. Tissue damage may occur due to an "unsteady" injection. Reflux of the drug may also occur when the needle is removed from the eye.

Other known devices include an electromechanical actuator to generate linear displacement of a piston, which in turn engages a plunger within a drug chamber. The plunger expels the drug formulation housed in the drug chamber through a needle. In such a design, a user activates a button through a controller that forces/instructs the actuator to move forward. While this design has more consistent flow rate control than the syringe design, such a system is costly and mechanically challenging to manufacture, especially for designs that include disposable tip segments that may be used with a reusable portion. Indeed, proper alignment of the actuator components between the disposable and reusable portions is critical, thereby requiring tight tolerances. Further, the electromechanical actuator arrangement also has an increased chance of failure in view of the additional moveable parts required. The electromechanical actuator assembly also adds both weight and length to the device.

BRIEF SUMMARY

Exemplary embodiments of a disposable injection device are disclosed herein. The disposable injection device comprises an annular sleeve, a predetermined pre-injection quantity of a substance configured for selective injection, and a temperature control element. The annular sleeve at least partially defines a dispensing chamber therein. The predetermined pre-injection quantity of the substance configured for selective injection is disposed within the dispensing chamber. The temperature control element is operably connected to the dispensing chamber, and is configured to selectively heat the substance to a predetermined temperature. The substance expands from the pre-injection quantity at the predetermined temperature to an injection quantity whereby the injection quantity is greater than a volume defined by the dispensing chamber. In this manner, a predetermined minimum quantity of the substance is self-expelled from the dispensing chamber. Methods of using the injection device are also disclosed.

BRIEF DESCRIPTION OF THE DRAWINGS

Embodiments of the present disclosure will now be described by way of example in greater detail with reference to the attached figures, in which.

DETAILED DESCRIPTION

Figure 1:
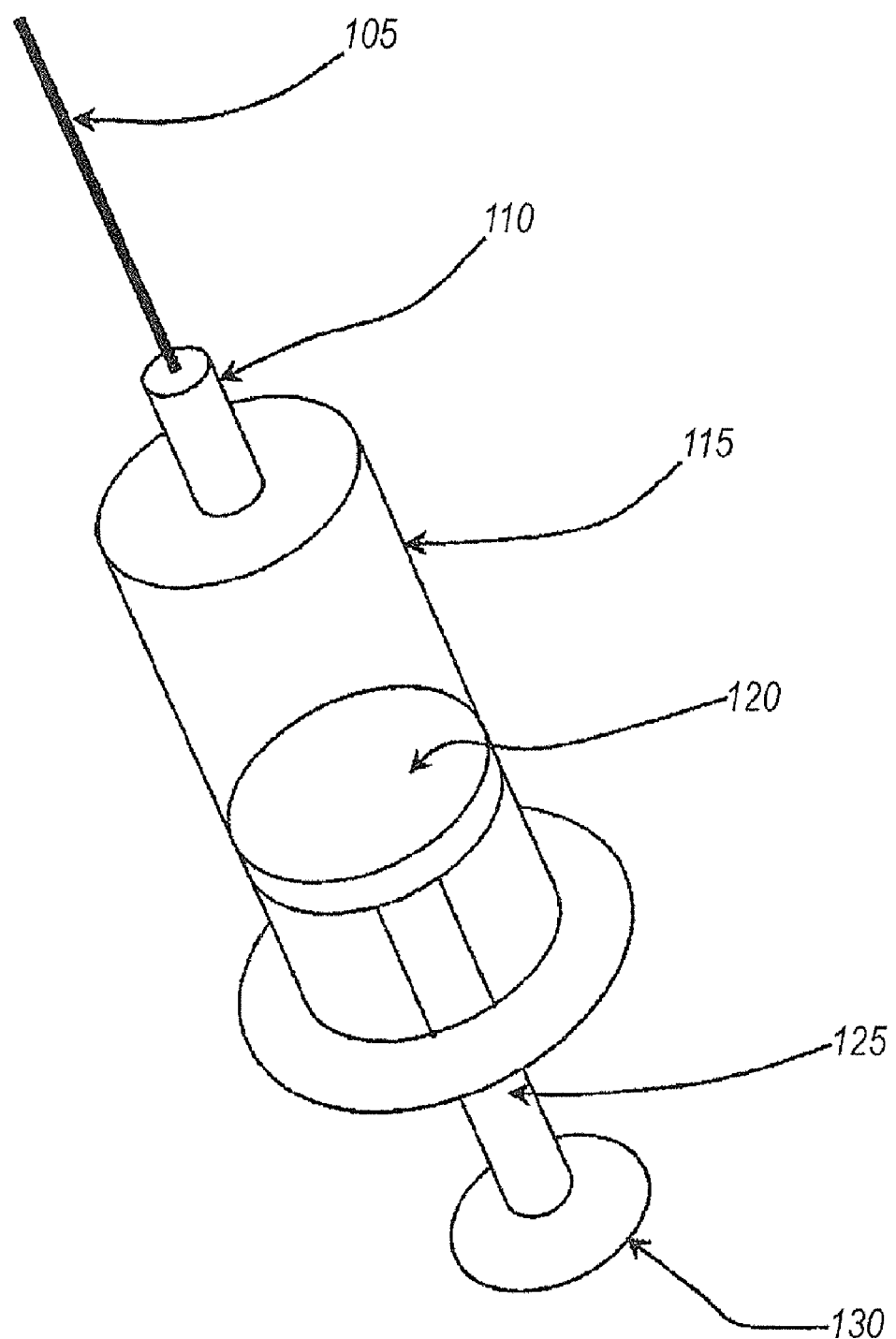
FIG. 1 is a perspective view of a prior art syringe.

Referring now to the discussion that follows and also to the drawings, illustrative approaches to the disclosed devices and methods are shown in detail. Although the drawings represent some possible approaches, the drawings are not necessarily to scale and certain features may be exaggerated, removed, or partially sectioned to better illustrate and explain the present disclosure. Further the descriptions set forth herein are not intended to be exhaustive or otherwise limit or restrict the claims to the precise forms and configurations shown in the drawings and disclosed in the following detailed description.

Figure 2:
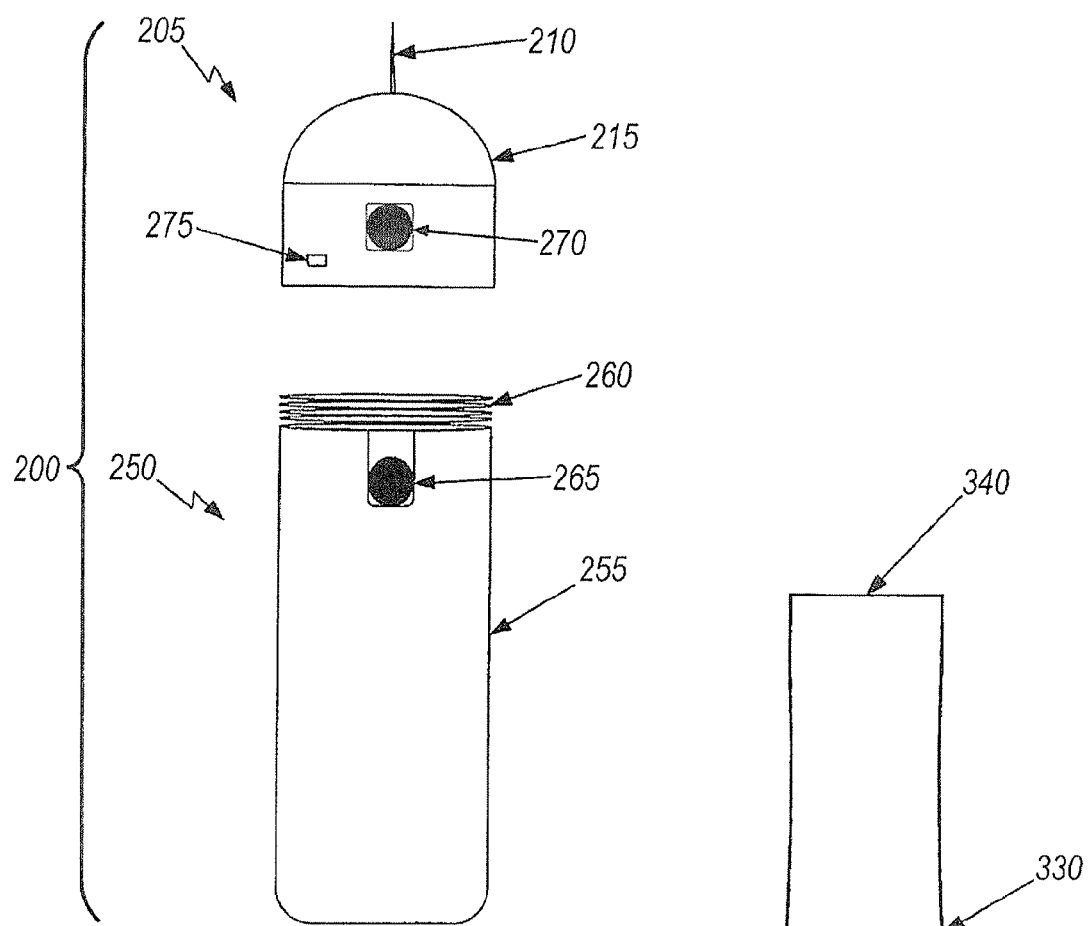
FIG. 2 is a partially exploded schematic view of an exemplary ophthalmic medical device including a disposable tip segment and a limited reuse assembly.

FIG. 2 is a partially exploded schematic of an exemplary arrangement of an ophthalmic medical device 200 that includes a disposable tip segment 205 and a limited reuse assembly 250. Disposable tip segment 205 comprises a needle 210, a housing 215, a button 270, and an optional light 275. The limited reuse assembly 250 comprises a housing 255, a lock mechanism 265, and an attachment portion 260.

Tip segment 205 is configured to be selectively connected to and removed from limited reuse assembly 250. In one exemplary arrangement, tip segment 205 has an attachment mechanism configured to mate with a corresponding attachment portion 260 formed on limited reuse assembly 250. In one exemplary arrangement, tip segment 205 is configured with a threaded attachment mechanism that mates with a corresponding threaded portion 260 of limited reuse assembly 250. In addition, a lock mechanism 265 may be used to secure tip segment 215 to limited reuse assembly 250. Lock mechanism 265 may be in the form of a button, a sliding switch, or a cantilevered mechanism. Other suitable mechanisms for connecting tip segment 205 to limited reuse assembly 250, such as those involving structural features that mate with each other, are commonly known in the art and are within the scope of the present disclosure.

Needle 210 is configured to deliver a substance, such as a drug, into an eye. Needle 210 may be of any known configuration. In one exemplary arrangement, needle 210 is designed such that its thermal characteristics are conductive to the particular drug delivery application. More specifically, needle may have a predetermined length conducive for delivering heated drug formulations.

Button 270 is configured to provide an input to the system. For example, button 270 may be used to activate the system to turn on a heater. Other switches, buttons or user-directed control inputs are commonly known and may be employed with limited reuse assembly 250 and/or tip segment 205.

Optional light 275 may be illuminated when tip segment is ready to be used. Optional light 275 may protrude outwardly from housing 215 or may be recessed therein. In the latter case, housing 215 may be provided with a transparent or translucent portion that permits a user to see optional light 275 when activated. In other embodiments, optional light 275 may be replaced by an indicator, such as a liquid crystal display, segmented display, or other device that indicates a status or condition of disposable tip segment 205. For example, optional light 275 may also pulse on and off to indicate other states, such as, but not limited to a system error, fully charged battery, insufficiently charged battery or faulty connection between the tip segment 205 and limited use assembly 250. While shown on tip segment 205, optional light 275 or other indicator may be located on limited reuse assembly 250.

Figure 3:
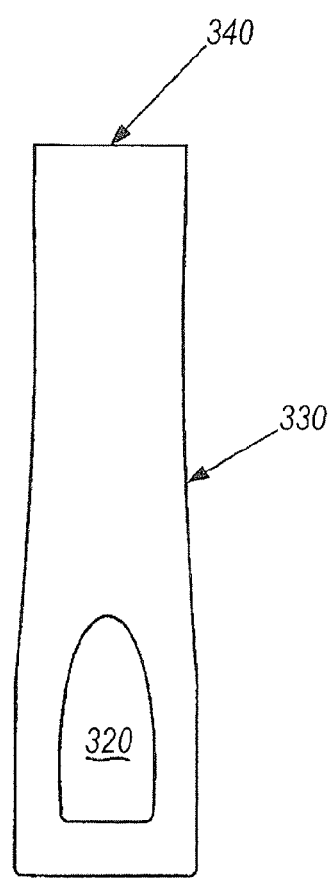
FIG. 3 is another embodiment of a limited reuse assembly.

FIG. 3 is another embodiment of a limited reuse assembly 250'. Limited reuse assembly 250' includes a display 320 and a housing 330. Disposable tip segment 205 attaches to an end 340 of limited reuse assembly 250'. Display 320 may be configured as a liquid crystal display, segmented display, or other device that indicates a status or condition of disposable tip segment 205 or limited reuse assembly 250'.

Figure 4:
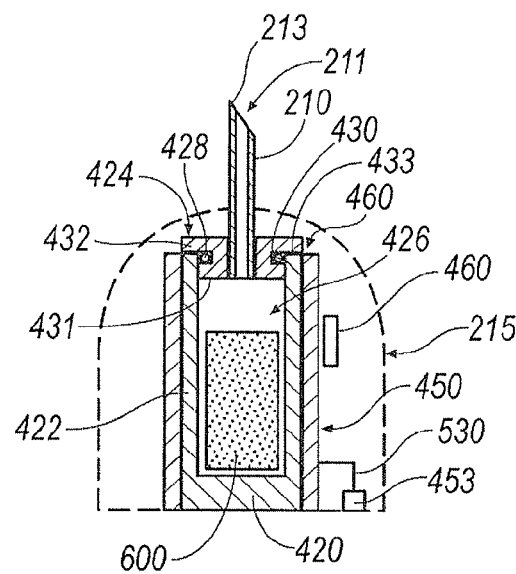
FIG. 4 is partial cross-sectional view of a disposable tip segment and a limited reuse assembly in accordance with an embodiment.
Figure 4:
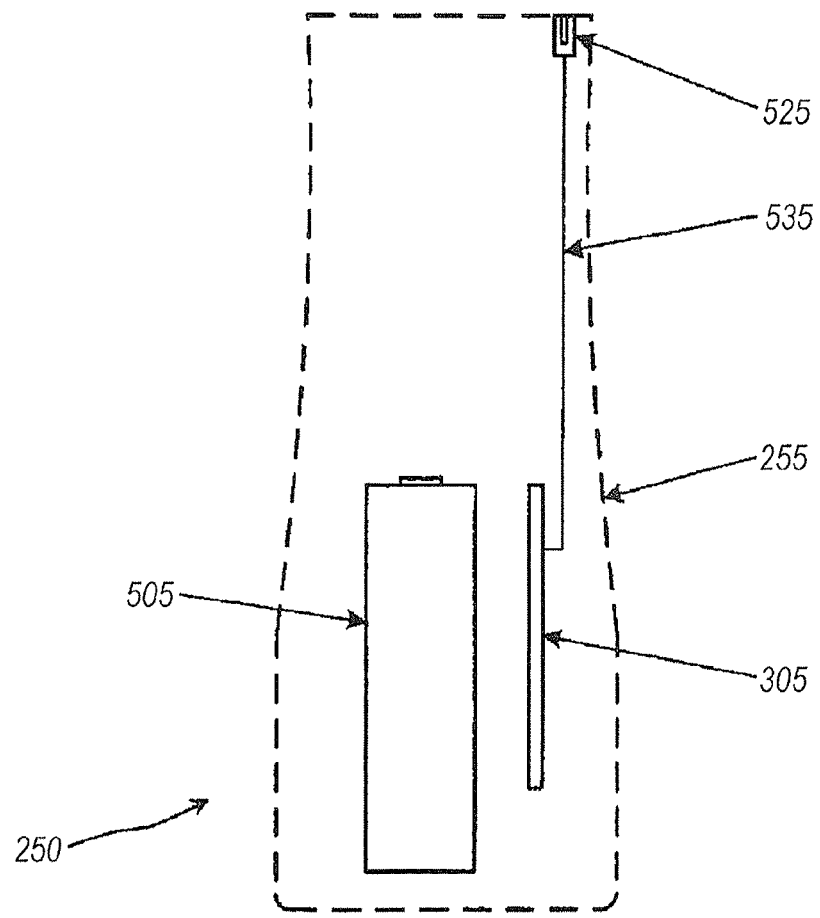

FIG. 4 is cross-sectional view of an exemplary arrangement of disposable tip segment 205 and limited reuse assembly 250. FIG. 4 schematically illustrates how tip segment 205 interfaces with limited reuse assembly 250. In the arrangement depicted in FIG. 4, tip segment 205 includes a dispensing chamber housing 425, tip segment housing 215, a temperature control device 450, thermal sensor 460, needle 210, an interface 530, and a tip interface connector 453. Limited reuse assembly 250 includes a power source 505, a controller 305, limited reuse assembly housing 255, interface 535, and limited reuse assembly interface connector 553.

In one exemplary configuration, dispensing chamber housing 425 includes a proximal end portion 420 that is connected to an annular sleeve 422 that extends away from proximal end portion 420. Dispensing chamber housing 425 is positioned within tip segment housing 215 with temperature control device 450 being at least partially disposed around an outside surface of dispensing chamber housing 425. A needle hub 424 is at least partially secured in a distal end 426 of annular sleeve 422. Needle hub 424 and annular sleeve 422 cooperate to form a dispensing chamber 426. In one exemplary configuration, temperature control device 450 may overlap needle hub 424 to apply heat and secure needle hub 424 to dispensing chamber housing 425 as a single assembly.

A seal member 428, such as an O-ring, is positioned between needle hub 424 and annular sleeve 422 to form a seal interface between annular sleeve 422 and needle hub 424. Seal member 428 prevents contamination of the drug formulation disposed within dispensing chamber 405. In one exemplary arrangement, needle hub 424 is configured with mounting grooves 430 that receive seal member 428. Other configurations for holding seal member 428 in place are also contemplated.

Needle hub 424 may be configured with an internal portion 431 and an external flange member 432. As may be seen in FIG. 4, internal portion 431 is sized to be received within distal end 426 of annular sleeve 422. Flange member 432 abuts against a distal end face 433 of annular sleeve 422, thereby limiting the depth that needle hub 424 may be inserted into annular sleeve 422.

Fixedly secured to needle hub 424 is needle 210. Needle 210 is generally hollow and defined by an open distal end 211 and an open proximal end 212. Distal end 211 may be configured with a piercing tip 213. Needle 210 is arranged within needle hub 424 such that proximal end 212 is arranged to be generally flush with a proximal end face 434 of needle hub 424. With needle hub 424 secured to annular sleeve 422, needle 210 is fluidly coupled to dispensing chamber 426.

Temperature control device 450 at least partially surrounds dispensing chamber housing 425. Temperature control device 450 is configured to heat dispensing chamber housing 425 and any substance contained therein, to be explained below in further detail. Interface 530 operably connects temperature control device 450 with tip interface connector 453.

Optional thermal sensor 460 provides temperature information to assist in controlling the operation of temperature control device 450. Thermal sensor 460 may be located near dispensing chamber housing 425 and measure a temperature near dispensing chamber housing 425. Alternatively, thermal sensor 460 may be located in thermal contact with dispensing chamber housing 425, in which case it measures a temperature of dispensing chamber housing 425. Thermal sensor 460 may be any of a number of different devices that can provide temperature information. For example, and without limitation, thermal sensor 460 may be a thermocouple or a resistive device whose resistance varies with temperature. Thermal sensor 460 is also electrically coupled to interface 530 or other similar interface.

The components of tip segment 205, including dispensing chamber housing 425, temperature control device 450 and needle hub 424 are at least partially enclosed by tip segment housing 215.

A power source 505 is disposed in limited reuse assembly 250. In limited reuse assembly 250, power source 505 is typically a rechargeable battery, such as a lithium ion battery, although other types of batteries may be employed. In addition, any other type of power cell is appropriate for power source 505. Power source 505 provides current to temperature control device 450 to heat dispensing chamber housing 425. Power source 505 may be configured for selective removal from housing 255 through a door or other similar feature for recharging.

Controller 305 is connected via interface 535 to limited reuse assembly interface connector 553. Limited reuse assembly interface connector 553 is located on an end surface 534 of limited reuse assembly housing 255. In this manner, limited reuse assembly interface connector 553 is configured to be operably connected with tip interface connector 453.

An interface between power source 505 and controller 305 allows controller 305 to control operation of power source 505. In such a case, controller 305 may control the charging and the discharging of power source 505 when power source 505 is a rechargeable battery.

Controller 305 is typically an integrated circuit with power, input, and output pins capable of performing logic functions. In various embodiments, controller 305 is a targeted device controller. In such a case, controller 305 performs specific control functions targeted to a specific device or component, such as a temperature control device or a power supply. For example, a temperature control device controller has the basic functionality to control a temperature control device. In other embodiments, controller 305 is a microprocessor. In such a case, controller 305 is programmable so that it can function to control more than one component of the device. In other cases, controller 305 is not a programmable microprocessor, but instead is a special purpose controller configured to control different components that perform different functions. While depicted as one component in FIG. 5, controller 305 may be made of many different components or integrated circuits.

Tip segment 205 is adapted to mate with or attach to limited reuse assembly 250. Tip interface connector 453 is adapted to connect with limited reuse assembly interface connector 553. When tip segment 205 is connected to limited reuse assembly 250 in this manner, an interface is formed between controller 305 and temperature control device 450. A signal can pass from controller 305 to temperature control device 450 through interface 535, limited reuse assembly interface connector 553, tip interface connector 453, and interface 530.

In accordance with one aspect of the disclosure, disposed within dispensing chamber 405 is a substance 600 to be delivered into an eye. In one exemplary arrangement, substance 600 is a drug suspended in a phase transition compound. The phase transition compound is in a solid or semi-solid state at lower temperatures and in a more liquid state at higher temperatures. Further, the phase transition compound has a first predefined volume at lower temperatures, wherein the compound is configured to fit within dispensing chamber 426 in a "static" or "pre-injection" configuration, and a second predefined volume at higher temperatures whereby the compound expands. In one exemplary embodiment, dispensing chamber 426 is sized such that the pre-injection configuration of the compound substantially fills dispensing chamber 426. Indeed, dispensing chamber 426 may be configured such that the compound completely fills dispensing chamber 426 in the pre-injection configuration. Alternatively, as shown in FIG. 4, dispensing chamber 426 is configured with an optional air gap such that substance 600 does not fill dispensing chamber 426 when in the pre-injection configuration. Further, in one exemplary arrangement, substance 600 is designed to expand to approximately 20% of its original volume upon application of heat, less the volume of any dead space from the air gap in dispensing chamber 424 and in the lumen of needle 210.

In accordance with the disclosure, to expel substance 600 from dispensing chamber 426 and into the eye, substance 600 is heated by the application of current to temperature control device 450. The application of heat causes substance 600' to expand (see FIG. 5) until substance 600" is forced to expel out through a lumen of needle 210 (see FIG. 6). In this manner, a medical device 200 is provided that does not require an electromechanical actuator or associated controller to expel drug substance 600 from the device 200. Nor is a plunger required to expel the drug substance from the device 200. Accordingly, a smaller and lighter device 200 may be provided, which has a simpler configuration that reduces the number of moving parts that may fail due to respective limited life cycles and eliminates critical alignment issues of an actuation device. Moreover, the rate at which the substance 600 may be selectively delivered to the eye may be controlled by controlling the application of heat and the pre-injection volume of substance 600.

A method for delivering a substance 600 to an eye will now be discussed. First, tip segment 205 is preloaded with substance 600 in a pre-injection configuration. More specifically, substance 600 is disposed within dispensing chamber 426. Tip segment 205 is then connected to limited reuse assembly 250. Needle 210 is positioned within the eye. An activation button 270 is then actuated (such as depressing button 270) to activate temperature control device 450 to start a rapid heating cycle. Temperature control device 450 serves to heat substance 600 to within a predetermined temperature range so as to activate a pre-determined expansion characteristic of the substance 600. Thermal sensor 460 provides temperature information to controller 305 to control temperature control device 450 to expand substance 600 sufficient to cause it to expel from dispensing chamber 424. Controller 305 can be programmed with information concerning the volume of dispensing chamber 424, the volume of the lumen of needle 210 and the expansion characteristics of substance 600 so as to calculate an appropriate temperature range for temperature control device 450 to generate sufficient heat to expand substance 600 sufficiently to expel a minimum volume of substance 600 from dispensing chamber 424.

In one embodiment, prior to needle 210 piercing the eye, a pre-heat cycle may be employed. In such a pre-heat cycle, substance 600' is expanded sufficient to fill drug dispensing chamber 424, without forcing substance 600' to exit through needle 210 (see FIG. 5). Use of a pre-heat cycle serves to keep the temperature of needle 210 as low as possible prior to injection, but decreases expulsion time once needle 210 is properly positioned within the eye. An indicator may signal to the user once a pre-heat cycle is completed such that once it reaches that state, needle 210 pierces the eye and dispensing chamber 424 is heated to a sufficient temperature to further expand substance 600" so as to expel substance 600" from medical device 210.

Figure 7:
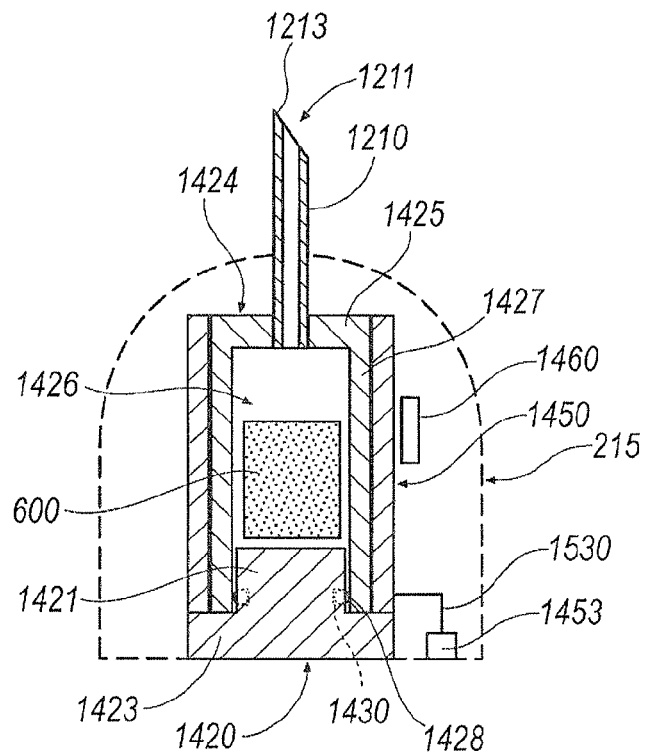
FIG. 7 is a partial cross-sectional view of an alternative embodiment of a disposable tip segment.
Figure 8:
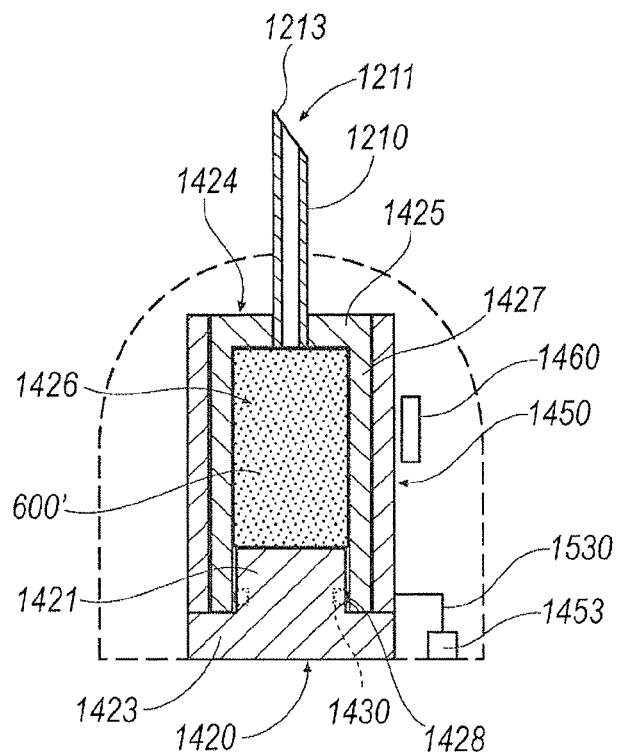
FIG. 8 is a partial cross-sectional view of the disposable tip segment of FIG. 7 during a heating cycle.
Figure 9:
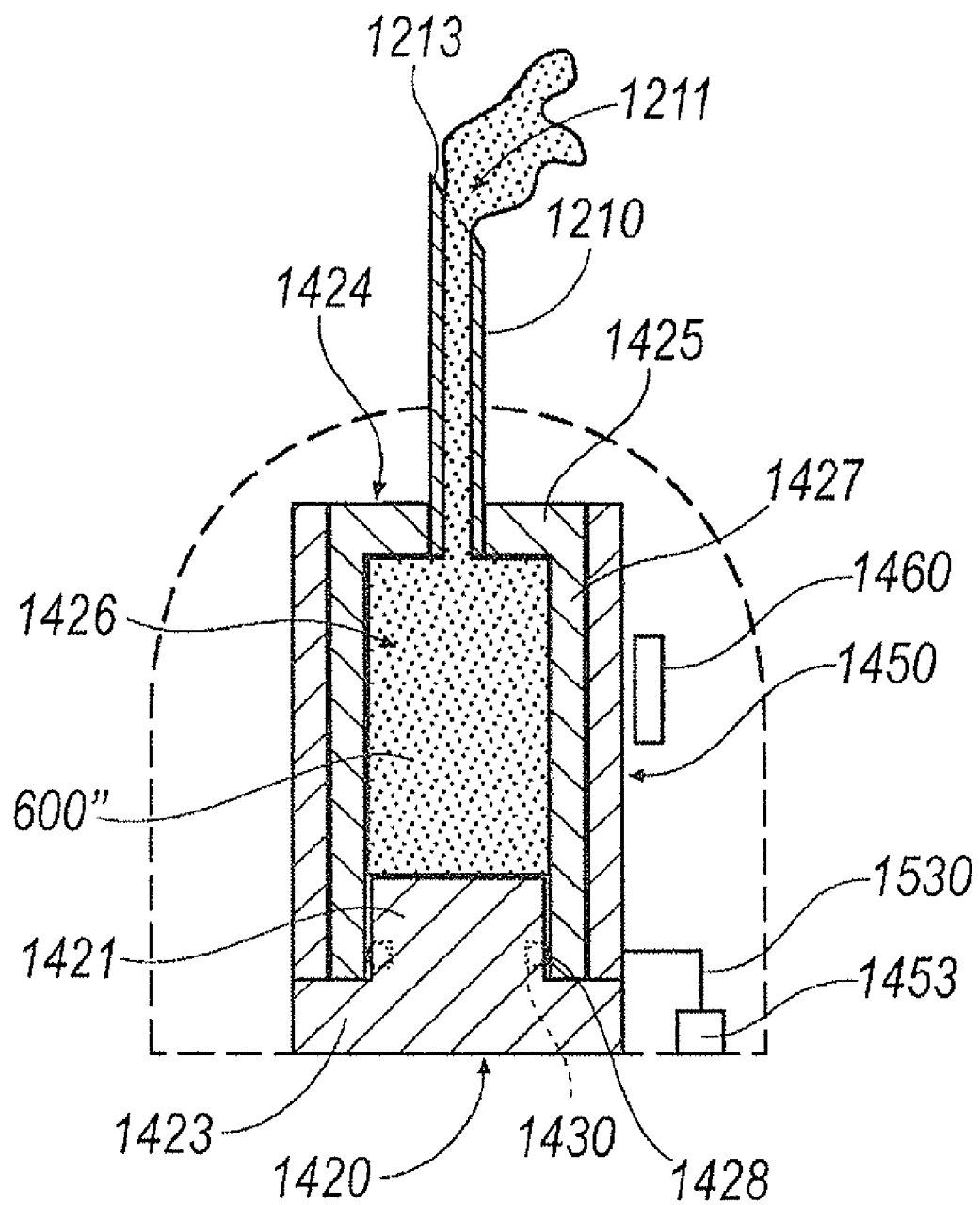
FIG. 9 is a partial cross-sectional view of the disposable tip segment of FIG. 7 during an expulsion heating cycle.

An alternative embodiment of a tip segment 1205 is shown in FIGS. 7-9. FIG. 7 is cross-sectional view of an exemplary arrangement of disposable tip segment 1205 that may be used with limited reuse assembly 250. In the arrangement depicted in FIG. 7, tip segment 1205 includes an axially extending needle hub 1424, a tip segment housing 1215, a temperature control device 1450, a thermal sensor 1460, a needle 1210, a dispensing chamber plug 1420, an interface 1530, and a tip interface connector 1453.

In one exemplary configuration, axially extending needle hub 1424 includes a distal end portion 1425 that is connected to an axially extending annular sleeve 1427 that extends away from distal end portion 1425. Annular sleeve 1427 is positioned within tip segment housing 1215 with temperature control device 1450 being at least partially disposed around an outside surface of annular sleeve 1127. Dispensing chamber plug 1420 is at least partially secured in a proximal end of annular sleeve 1427. Dispensing chamber plug 1420 and annular sleeve 1427 cooperate to form a dispensing chamber 1426. In one exemplary embodiment, dispensing chamber plug 1420 is configured from an elastomer material so as to sealingly engage with annular sleeve in a press-fit manner. In an alternative arrangement, a seal member 1428, such as an O-ring, is positioned between dispensing chamber plug 1420 and annular sleeve 1427 to form a seal interface therebetween. By sealing dispensing chamber 1426, contamination of the drug formulation contained within dispensing chamber 1426 is prevented. In one exemplary arrangement, dispensing chamber plug 1420 is configured with a mounting groove 1430 (shown in phantom) that receives seal member 1428. Other configurations for holding seal member 1428 in place are also contemplated.

Dispensing chamber plug 1420 may be configured with an internal portion 1421 and an external flange member 1423. As may be seen in FIG. 7, internal portion 1421 is sized to be received within the open proximal end of annular sleeve 1427. Flange member 1423 abuts against a proximal end face of annular sleeve 1427, thereby limiting the depth that dispensing chamber plug 1420 may be inserted into annular sleeve 1427.

Fixedly secured to distal end portion 1425 of needle hub 1424 is needle 1210. Needle 1210 is generally hollow and defined by an open distal end 1211 and an open proximal end 1212. Distal end 1211 may be configured with a piercing tip 1213. Needle 1210 is arranged within needle hub 1424 such that proximal end 1212 is arranged to be generally flush with a proximal end face 1434 of needle hub 1424 and in fluid communication with dispensing chamber 1426.

Temperature control device 1450 at least partially surrounds dispensing chamber 1426. Temperature control device 1450 is configured to heat annular sleeve 1427 and any substance contained in dispensing chamber 1426, to be explained below in further detail. Interface 1530 operably connects temperature control device 1450 with tip interface connector 1453.

Figure 5:
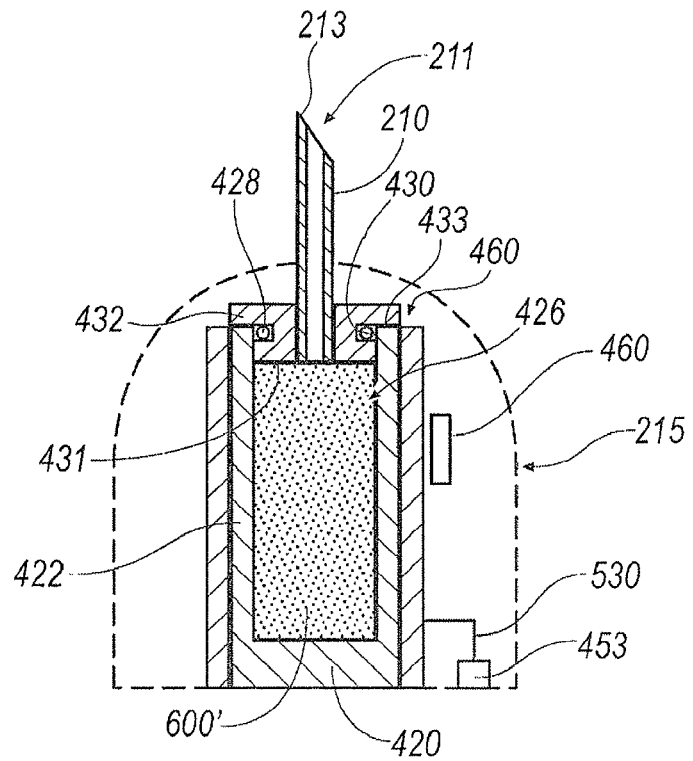
FIG. 5 is a partial cross-sectional view of the disposable tip segment of FIG. 4 during a heating cycle.
Figure 6:
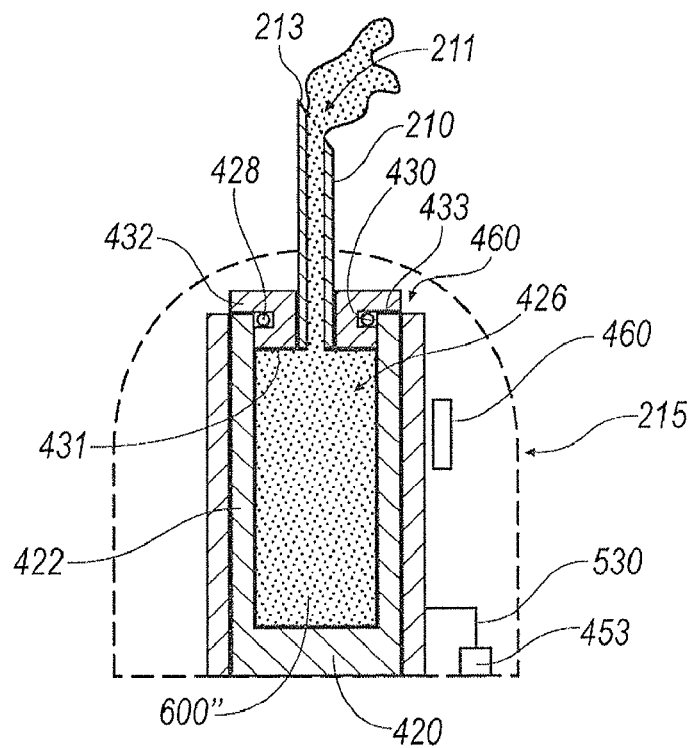
FIG. 6 is a partial cross-sectional view of the disposable tip segment of FIG. 4 during an expulsion heating cycle.

In accordance with one aspect of the disclosure, as with the embodiment shown in FIGS. 4-6, disposed within dispensing chamber 1426 is a substance 600 to be delivered into an eye. In one exemplary arrangement, substance 600 is a drug suspended in a phase transition compound. In one exemplary embodiment, dispensing chamber 1426 is sized such that the pre-injection configuration of the compound substantially fills dispensing chamber 1426. Indeed, dispensing chamber 1426 may be configured such that the compound completely fills dispensing chamber 1426 in the pre-injection configuration. Alternatively, as shown in FIG. 7, dispensing chamber 1426 is configured with an optional air gap such that substance 600 does not fill dispensing chamber 1426 when in the pre-injection configuration.

In accordance with the disclosure, to expel substance 600 from dispensing chamber 1426 and into the eye, substance 600 is heated by the application of current to temperature control device 1450. The heat application causes substance 600' to expand (see FIG. 8) until substance 600" is forced to expel out through a lumen of needle 1210 (see FIG. 9). In this manner, a medical device 1200 is provided that does not require an electromechanical actuator or associated controller to expel a drug substance 600 from the device 1200. Nor is a plunger required to expel the drug substance from the device 200. Accordingly, a lighter and smaller device 200 may be provided, that has a simpler configuration that reduces the number of moving parts that may fail due to respective limited life cycles and eliminates critical alignment issues of an actuation device.

A method delivering a substance 600 to an eye will now be discussed with respect to FIGS. 7-9. First, tip segment 1205 is preloaded with substance 600 in a pre-injection configuration and is disposed within dispensing chamber 1426. Tip segment 1205 is then connected to limited reuse assembly 250. Needle 1210 is positioned within the eye. An activation button (such as that shown as element 270 in FIG. 2) would then be actuated (such as being depressed) to activate temperature control device 1450 and start a rapid heating cycle. Temperature control device 1450 serves to heat substance 600 to within a predetermined temperature range so as to activate a pre-determined expansion characteristic of the substance 600. Thermal sensor 1460 provides temperature information to controller 1305 to control temperature control device 1450 to expand substance 600 sufficient to cause it to expel from dispensing chamber 1424. Controller 1305 can be programmed with information concerning the volume of dispensing chamber 1424, the volume of the lumen of needle 1210 and the expansion characteristics of substance 600 so as to calculate an appropriate temperature range for temperature control device 1450 to generate sufficient heat to expand substance 600 sufficiently to expel from dispensing chamber 1424.

In one embodiment, prior to needle 210 piercing the eye, a pre-heat cycle may be employed. In such a pre-heat cycle, substance 600' is expanded sufficient to fill drug dispensing chamber 1424, without exiting through needle 210 (see FIG. 8). An indicator may signal to the user once a pre-heat cycle is completed such that once ready, needle 1210 pierces the eye and the heating cycle is continued until dispensing chamber 1424 is heated to a sufficient temperature to further expand substance 600" so as to expel substance 600" from medical device 210.

It will be appreciated that the devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A disposable injection device comprising:
   a dispensing chamber housing at least partially defining a dispensing chamber therein, wherein the dispensing chamber comprises an open distal end, configured to receive a needle hub, and a closed, fixed proximal end;
   a predetermined pre-injection quantity of a substance configured for injection disposed within the dispensing chamber; and
   a temperature control element operably connected to the dispensing chamber housing, wherein the temperature control element is configured to heat the substance to a predetermined temperature;
   wherein the substance expands from a pre-injection volume at the predetermined temperature to an injection volume whereby the injection volume is greater than a volume defined by the dispensing chamber such that a predetermined minimum quantity of the substance is self-expelled from the dispensing chamber.

2. The disposable injection device of claim 1, further comprising a needle fluidly coupled to the dispensing chamber, wherein the predetermined minimum quantity of the substance is self-expelled from the dispensing chamber through the needle.

3. The disposable injection device of claim 2, wherein the needle is fixedly positioned in the needle hub that cooperates with the dispensing chamber housing to form the dispensing chamber.

4. The disposable injection device of claim 3, wherein the dispensing chamber housing comprises an annular sleeve and wherein the needle hub is engaged with a distal end of the annular sleeve.

5. The disposable injection device of claim 4, wherein the dispensing chamber housing comprises a closed proximal end portion integrally connected to the annular sleeve.

6. The disposable injection device of claim 5, wherein the needle hub further comprises an internal portion configured to be disposed within the distal end of the annular sleeve.

7. The disposable injection device of claim 6, wherein the internal portion further includes a mounting groove for receiving a sealing member.

8. The disposable injection device of claim 3, wherein the needle hub further comprises an external mounting flange, wherein the flange is configured to abut against a distal end face of the dispensing chamber housing.

9. The disposable injection device of claim 8, wherein the temperature control element at least partially extends around the dispensing chamber housing.

10. The disposable injection device of claim 9, wherein the temperature control element at least partially extends around the needle hub.

11. The disposable injection device of claim 1, wherein the dispensing chamber is sized such that an air gap is formed within the dispensing chamber when the pre-injection quantity of the substance is placed within the dispensing chamber.

12. The disposable injection device of claim 1, wherein the pre-injection quantity of the substance substantially fills the dispensing chamber.

13. The disposable injection device of claim 1, wherein the substance is a drug for treating a condition of the eye.

14. The disposable injection device of claim 1, wherein the injection volume is at least 20% greater than the pre-injection volume.

15. The disposable injection device of claim 1, wherein the dispensing chamber is housed within a tip segment and wherein the tip segment is attachable to a limited reuse assembly.

16. The disposable injection device of claim 15, further comprising an electrical interface for coupling the temperature control device to the limited reuse assembly.

17. A disposable injection device comprising:
    an annular sleeve at least partially defining a dispensing chamber therein, wherein the dispensing chamber comprises an open distal end, configured to receive a needle hub, and a closed, fixed proximal end;
    a predetermined pre-injection quantity of a substance configured for injection disposed within the dispensing chamber; and
    a temperature control element operably connected to the dispensing chamber, wherein the temperature control element is configured to heat the substance to a predetermined temperature;
    wherein the substance expands from a pre-injection volume at the predetermined temperature to an injection volume whereby the injection volume, greater than a volume defined by the dispensing chamber such that a predetermined minimum quantity of the substance is self-expelled from the dispensing chamber.

18. The disposable injection device of claim 17, further comprising a needle fluidly coupled to the dispensing chamber.

19. The disposable injection device of claim 18, wherein the annular sleeve is integrally connected distal end portion and the needle is fixedly positioned in the distal end portion.

20. The disposable injection device of claim 19, further comprising a dispensing chamber plug that cooperates with the annular sleeve to form the dispensing chamber.

* * * * *